US00PP37691P2

(12) United States Plant Patent
Ranney et al.

(10) Patent No.: US PP37,691 P2
(45) Date of Patent: Sep. 8, 2026

(54) ***RUDBECKIA* PLANT NAMED 'NCRH2'**

(50) Latin Name: ***Rudbeckia* spp.**
Varietal Denomination: NCRH2

(71) Applicant: North Carolina State University, Raleigh, NC (US)

(72) Inventors: Thomas Ranney, Arden, NC (US); Nathan P. Lynch, Mills River, NC (US); Irene Palmer, Mills River, NC (US); Andra Windorf Nus, Mills River, NC (US); John Tyler Nix, Mills River, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 19/339,428

(22) Filed: Sep. 25, 2025

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./474
See application file for complete search history.

(56) References Cited

U.S. PATENT DOCUMENTS

PP28,498 P2 * 10/2017 Horvath ..... A01H 5/02
Plt./321

* cited by examiner

*Primary Examiner* — Susan McCormick Ewoldt
*Assistant Examiner* — Zachariah Allan Kay
(74) *Attorney, Agent, or Firm* — Myers Bigel, P.A.

(57) ABSTRACT

A new and distinct variety of *Rudbeckia* plant as illustrated and described, characterized by the combination of distinctive bicolor flowers with red at the base of each petal and yellow at the tips when in full bloom and a compact, upright habit.

3 Drawing Sheets

Latin name: The Latin name of the novel plant variety disclosed herein is *Rudbeckia* spp.

Variety denomination: The inventive cultivar of *Rudbeckia* disclosed herein has been given the varietal denomination 'NCRH2.'

BACKGROUND OF THE INVENTION

The present invention comprises a new and distinct *Rudbeckia* plant, referred to hereinafter by the cultivar name 'NCRH2.' This new *Rudbeckia* was developed through a breeding program at a research nursery located in Mills River, North Carolina. 'NCRH2' is a plant from an interspecific, tetraploid *Rudbeckia* hybrid isolated in a block of similar hybrids.

The first asexual propagation of 'NCRH2' was carried out in February 2018 by crown divisions in Mills River, North Carolina and has been asexually reproduced repeatedly by division over a seven-year period. 'NCRH2' has been found to retain its distinctive characteristics through successive asexual propagations.

SUMMARY OF THE INVENTION

The following are the unique combination of characteristics of this new cultivar that distinguish 'NCRH2' from all other varieties of *Rudbeckia* when grown under standard horticultural practices at Mills River, North Carolina.

1. 'NCRH2' exhibits distinctive bicolor flowers with red at the base of each petal and yellow at the tips when in full bloom.

2. 'NCRH2' exhibits a compact, upright habit.
3. 'NCRH2' is a cold-hardy, perennial.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which more accurately describe the colors of the new *Rudbeckia* 'NCRH2.'

DETAILED BOTANICAL DESCRIPTION OF THE NEW VARIETY

Figure 1:
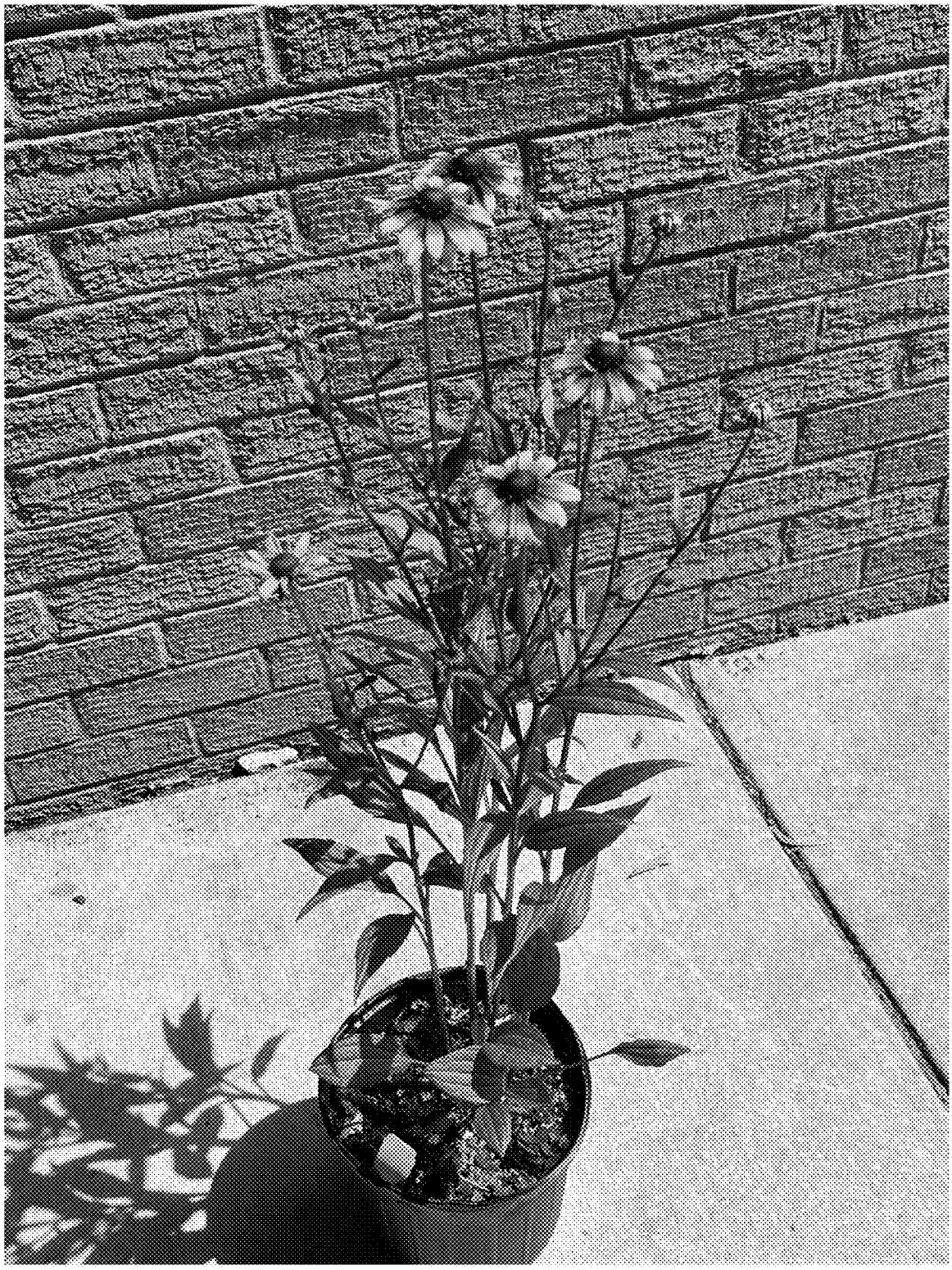
FIG. 1 is a color photograph showing the habit of a three-year-old container-grown plant of 'NCRH2' in the summer of 2024 in Mills River, North Carolina.
Figure 2:
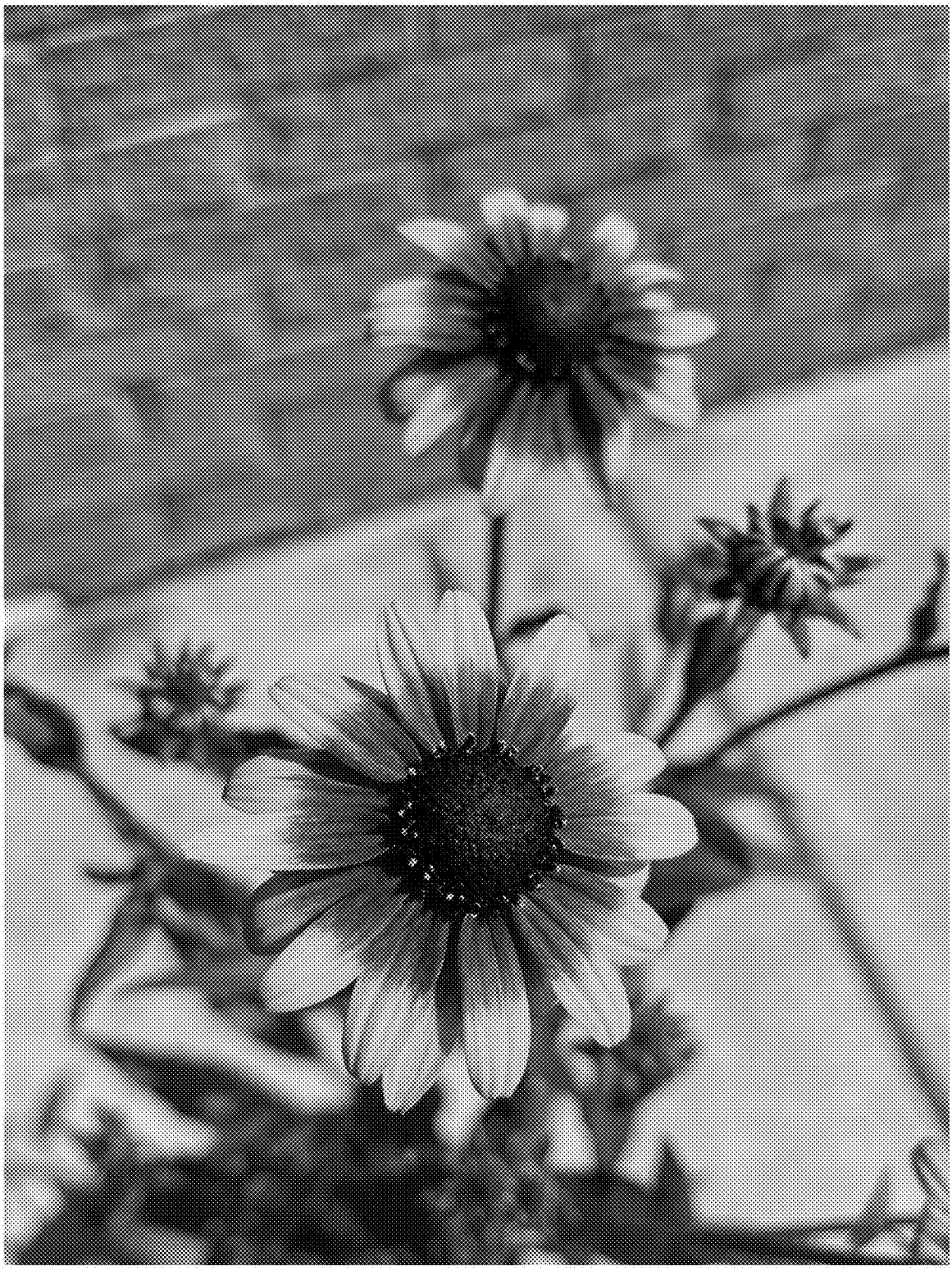
FIG. 2 is a color photograph of the inflorescence of a three-year-old container-grown plant of 'NCRH2' in the summer of 2024 in Mills River, North Carolina.
Figure 3:
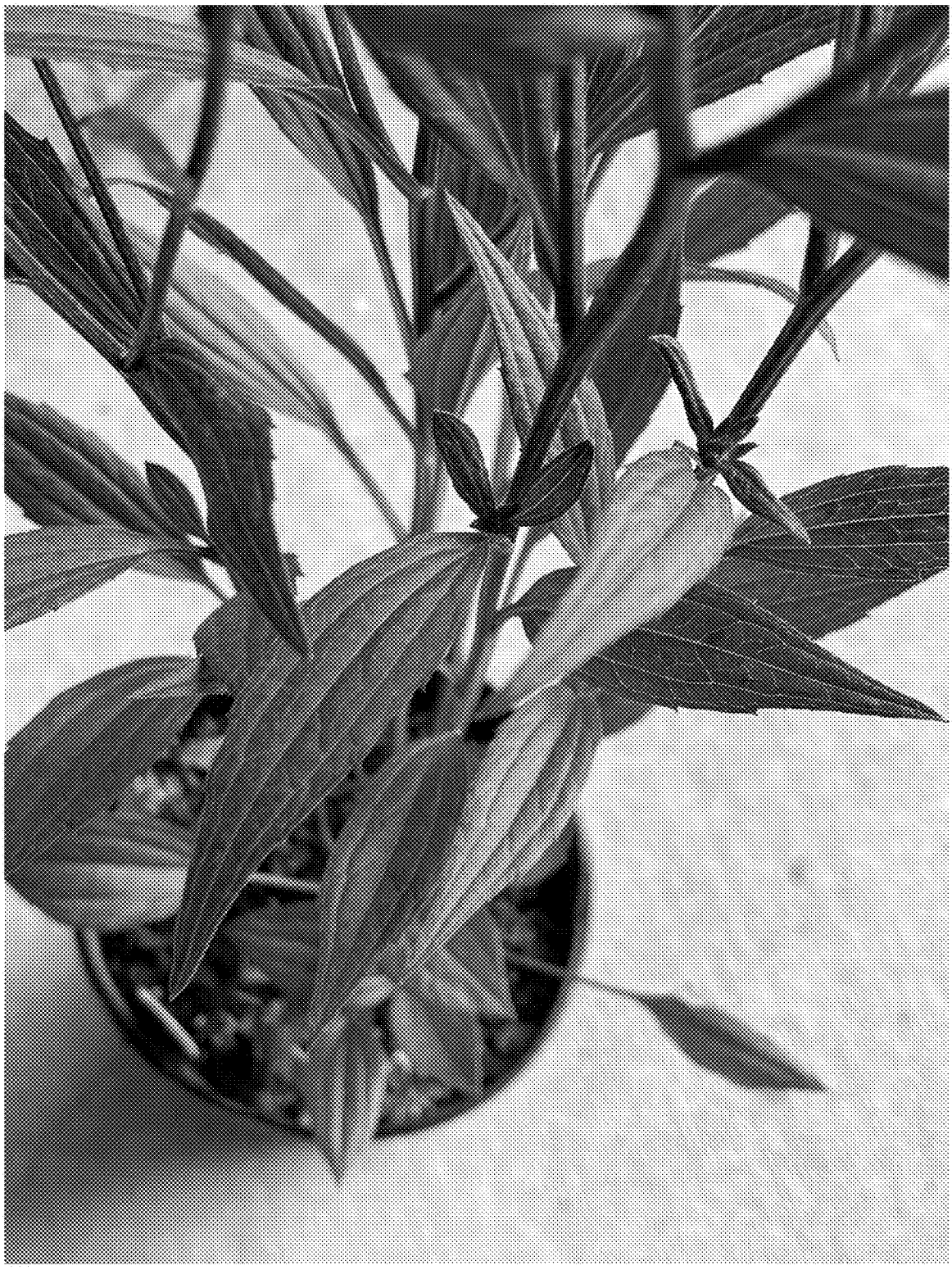
FIG. 3 is a color photograph of the foliage of a three-year-old container-grown plant of 'NCRH2' in the summer of 2024 in Mills River, North Carolina.

The following is a detailed description of the botanical characteristics of a new and distinct cultivar of *Rudbeckia* plant known by the cultivar name 'NCRH2.' The detailed description was taken on a three-year-old container-grown plant in Mills River, North Carolina in 2024. All colors cited herein refer to The Royal Horticulture Society Colour Chart designations (The Royal Horticultural Society, London, 2001, $4^{th}$ ed.) except where general terms of ordinary dictionary significance are used. Where dimensions, sizes, colors, and other characteristics are given, it is to be understood that such characteristics are approximations or averages set forth as accurately as practicable.

The descriptions reported herein are from a three-year-old container-grown plant. Plant measurements were taken in in the summer of 2024 in Mills River, North Carolina. *Rudbeckia* 'NCRH2' has not been observed under all possible environmental conditions; therefore, the phenotype may vary under different environmental conditions such as season, temperature, light intensity, day length, cultural conditions, and the like, without however, any variance in the genotype.

Classification:

*Botanical name.*—*Rudbeckia.*

*Common name.*—Black-eyed Susan.

*Variety name.*—'NCRH2.'

Parentage: Selected from a population of open-pollinated, tetraploid, interspecific hybrid seedlings of *Rudbeckia* H2014-233 (unpatented) that was isolated in a block of similar hybrids.

Plant Description:

*Bloom period.*—July to August in Mills River, North Carolina.

*Duration of bloom time from bud break to anthesis.*—7 to 14 days, outdoors, in Mills River, North Carolina.

*Growth habit.*—Herbaceous perennial, upright habit.

*Height.*—Reaches about 65 cm in full bloom.

*Spread.*—Reaches about 25 cm.

Growth and propagation:

*Growth.*—Average growth rate reaching 65 cm in one growing season.

*Propagation.*—Vegetative division, shoot cuttings, and micropropagation.

Stem description:

*Primary stem diameter.*—0.5 cm to 0.6 cm.

*Primary stem color.*—Moderate Yellow Green (RHS 146C).

*Primary stem texture.*—Pubescent.

*Primary stem internode length.*—About 4.7 cm.

*Secondary stem description.*—Average 5 lateral stems per primary stem.

*Secondary stem length.*—About 17.8 cm.

*Secondary stem diameter.*—About 0.6 cm.

*Secondary stem color.*—Moderate Yellow Green (RHS 148A).

*Secondary stem texture.*—Pubescent.

Stem foliage:

*Type.*—Herbaceous.

*Arrangement.*—Alternate, simple.

*Lamina length.*—About 8.4 cm.

*Lamina width.*—About 2.7 cm.

*Shape.*—Lanceolate.

*Apex.*—Acuminate.

*Base.*—Attenuate.

*Margins.*—Dentate.

*Texture.*—Pubescent.

*Color.*—Greyish Olive Green (RHS NN137B).

*Venation.*—Pinnate. Vein color: Moderate Yellow Green (RHS 148B).

*Leaf attachment.*—Petiolate.

*Petiole.*—Length: About 5.2 cm. Diameter: About 0.2 cm. Color: Moderate Olive Green (RHS 146A). Texture: Pubescent.

Basal foliage:

*Lamina length.*—About 10 cm.

*Lamina width.*—About 5.5 cm.

*Shape.*—Ovate.

*Apex.*—Obtuse.

*Base.*—Acute.

*Margins.*—Dentate.

*Texture.*—Pubescent.

*Color.*—Greyish Olive Green (RHS NN137B).

*Venation.*—Pinnate. Vein color: Moderate Yellow Green (RHS 148B).

*Leaf attachment.*—Petiolate.

*Petiole.*—Length: About 11 cm. Diameter: About 0.2 cm. Color: Moderate Olive Green (RHS 146A). Texture: Pubescent.

Inflorescence:

*Description.*—Single, composite flowers with ray and disc florets, borne on both terminal and axillary peduncles.

*Number of inflorescences per plant.*—About 25.

*Bud.*—Shape: Oblate. Length: About 0.8. Diameter: About 1.3 cm. Color: Moderate Yellow Green (RHS 146D).

*Overall inflorescence size.*—Diameter: 6.0 cm. Height: About 2.5 cm. Disc size: Height at anthesis: About 2.0 cm. Width: About 1.8 cm.

*Disc floret.*—Number: About 500 florets. Shape: Cylindrical. Length: 0.6 cm. Width: 0.1 cm. Mature color: Dark Greyish Purple (RHS 202A).

*Ray floret.*—Number: About 16 per inflorescence. Corolla length: About 2.1 cm. Corolla width: About 0.7 cm. Corolla shape: Lanceolate. Corolla margin: Entire. Corolla apex: Emarginate. Corolla base: Cuneate. Corolla texture: Glabrous. Corolla color upon opening: Adaxial (upper surface) color: Vivid Yellow (RHS 14A). Abaxial (lower surface) color: Vivid Yellow (RHS 14B). Mature corolla color: Adaxial color: Proximal end Dark Reddish Orange (RHS 175B) blending to distal end Vivid Yellow (RHS 14A). Abaxial (lower surface) color: Vivid Yellow (RHS 14B). Corolla color at anthesis: Adaxial color: Proximal end Moderate Orange (RHS N172D) blending to distal end Vivid Yellow (RHS 14A). Abaxial color: Vivid Yellow (RHS 14B).

*Phyllaries.*—Number per inflorescence: About 16. Shape: Lanceolate. Length: About 1.0 cm. Width: About 0.3 cm. Apex: Mucronate. Base: Truncate. Margin: Entire. Color: Greyish Olive Green (RHS NN137B). Texture: Pubescent.

*Peduncles.*—Length: About 14.0 cm. Diameter: 0.2 cm. Texture: Pubescent. Color: Greyish Olive Green (RHS NN137B).

Reproductive organs:

*Gynoecium.*—Pistil number: 1. Pistil length: 0.4 cm. Stigma shape: Two-parted, linear. Stigma color: Dark Greyish Purple (RHS 202A). Style length: 0.4 cm. Style color: Light Greenish Yellow (RHS 2D).

*Androecium.*—Stamen number: 5. Filament color: Dark Greyish Purple (RHS 202A). Filament length: 0.4 cm. Anther shape: Oblong. Anther length: 0.1 cm. Anther color: Dark Greyish Purple (RHS 202A). Amount of pollen: Scarce.

Fruit and seed: None observed.

Cold hardiness: At least U.S.D.A. Zone 6B; testing has not been completed in colder zones.

Disease and insect resistance: Resistance to diseases common to *Rudbeckia* has not been observed on plants grown under nursery conditions.

Comparison with other *Rudbeckia* cultivars. 'NCRH2' is distinguished from *Rudbeckia* 'American Gold Rush' (U.S. Plant Pat. No. 28,498) in that 'NCRH2' has bicolored flowers of yellow and red, and a taller (65 cm) habit, whereas *Rudbeckia* 'American Gold Rush' has yellow flowers and a shorter (36 cm) habit. 'NCRH2' is distinguished from *Rudbeckia* 'Goldsturm' (not patented) in that 'NCRH2' has multicolored flowers whereas 'Goldsturm' has yellow flowers. 'NCRH2' is distinguished from *Rudbeckia* 'Glitters Like Gold' (U.S. Plant Pat. No. 30,933) in that 'NCRH2' has a shorter (65 cm) habit than 'Glitters Like Gold' (90 cm).

We claim:

1. A new and distinct *Rudbeckia* plant named 'NCRH2,' substantially as illustrated and described herein.

* * * * *